United States Patent [19]
Christy

[11] Patent Number: 5,803,922
[45] Date of Patent: Sep. 8, 1998

[54] ENDOSCOPIC WOUND ACCESS, ANCHORING, AND INSUFFLATION DEVICE AND METHOD

[76] Inventor: William J. Christy, 1325 Sunset Dr., Winter Park, Fla. 32789

[21] Appl. No.: 794,731

[22] Filed: Feb. 3, 1997

Related U.S. Application Data

[63] Continuation-in-part of Ser. No. 495,179, Jun. 27, 1995, Pat. No. 5,683,378.
[51] Int. Cl.$^6$ .................................................. A61B 17/00
[52] U.S. Cl. .............................. 606/1; 606/108; 606/185; 606/213; 600/201; 600/207
[58] Field of Search ................................ 606/1, 108, 185, 606/213; 604/167, 169, 174, 178, 264; 600/201, 207

[56] References Cited

U.S. PATENT DOCUMENTS

| | | | |
|---|---|---|---|
| 4,921,479 | 5/1990 | Grayzel | 606/108 |
| 5,322,516 | 6/1994 | Brugger | 606/264 |
| 5,441,487 | 8/1995 | Vedder | 606/167 |
| 5,490,843 | 2/1996 | Hildwein et al. | 606/185 |

*Primary Examiner*—Michael Buiz
*Assistant Examiner*—Daphna Shal
*Attorney, Agent, or Firm*—Allen, Dyer, Doppelt, Milbrath & Gilchrist, P.A.

[57] ABSTRACT

A device for insufflating a body cavity preparatory to and during an intracavity procedure is provided that includes a generally cylindrical body anchorable to skin surrounding an incision into the body cavity. An elevation member permits the lifting of the device, along with the attached skin, in a proximal direction, allowing mechanical insufflation. The bore is sealable in order to maintain insufflation during insertion of a surgical implement. The method includes the steps of inserting the device into the incision, anchoring the cylindrical body to the skin, elevating the cylindrical body in a proximal direction, thereby mechanically insufflating the body cavity, and sealing the bore to admit and closely surround the surgical implement for maintaining insufflation. Then a surgical implement can be inserted into the bore of the device and the surgical procedure performed.

19 Claims, 6 Drawing Sheets

ENDOSCOPIC WOUND ACCESS, ANCHORING, AND INSUFFLATION DEVICE AND METHOD

CROSS-REFERENCE TO RELATION APPLICATION

This application is a continuation-in-part of application Ser. No. 08/495,179, "Endoscopic Wound Access and Anchoring Device and Method," filed Jun. 27, 1995 now U.S. Pat. No. 5,683,378.

BACKGROUND OF THE INVENTION

1. Field of the Invention

This invention relates generally to the field of surgical devices and, more particularly, to surgical cannula devices used as portals to body cavities in laparoscopic and endoscopic applications and to methods and devices for insufflating a body cavity.

2. Description of Related Art

Laparoscopic or endoscopic surgical procedures are now widely used in many specialties in the surgical community. These procedures generally involve a "C"-shaped incision through the navel, through skin, adipose tissue, fascia, muscle, and peritoneum, which comprise the abdomninal wall or thoracic wall. Using this method many organs of the gut may be viewed and operated upon: gall bladder, intestines, appendix, uterus, fallopian tubes, ovaries, and lungs.

Trocars, pointed cannulae with pointed obturators for piercing the wall of a cavity, are often used to create ports through which surgical instruments may be passed, instead of making long incisions in the abdominal or thoracic wall. The diameter of the trocar differs based upon the procedure to be performed, and may range from 3 to 33 millimeters.

Once the puncture has been made, the pointed trocar is usually removed, and the cannula is then utilized as a port through which instruments and viewing devices may be passed into the body cavity.

Laparoscopic or endoscopic procedures generally entail the introduction of elevated-pressure gas into the body cavity being operated upon. This enables the surgeon to visualize the area better and also provides additional room in which to work. Significant leakage of gas pressure would cause the area to collapse, disturbing and delaying the procedure, which could be dangerous. Such a leakage can occur, for instance, during a change of instruments through a cannula or trocar, or during suturing, after a trocar has been removed.

It is known to use a gasket at the proximal end of a cannula to prevent loss of pressure; however, gas may also leak out from around the exterior of the cannula.

Another difficulty in procedures such as those involving multiple cannulae is that one may be easily disturbed while moving about the external area.

Several trocar stabilizers are known in the art, including those taught by Banks et al. (U.S. Pat. No. 5,364,367), Tal et al. (U.S. Pat. No. 5,366,446), Brinkerhoff et al. (U.S. Pat. No. 5,366,478), Shichman (U.S. Pat. No. 5,370,625), and Yoon (U.S. Pat. No. 5,375,588).

It is also known that the introduction of a gas into a body cavity can cause postoperative discomfort to the patient. [bill—are there other contraindications to the use of high-pressure gas insufflation? if so, please insert here]

SUMMARY OF THE PRESENT INVENTION

It is an object of the present invention to provide a cannula device for use in endoscopic and laparoscopic procedures that maintains insufflation within a body cavity during a surgical procedure.

It is another object to provide such a device that is anchorable to an external area of the surgical site.

It is an additional object to provide such a device that is usable as a mechanical insufflator.

It is a further object to provide a method of operating upon a body cavity while introducing and maintaining a desired level of insufflation within that cavity.

These and other objects are achieved with the following embodiments of the invention.

Device for Introducing and Maintaining Insufflation within a Body Cavity

The present invention comprises in one embodiment a means of introducing and maintaining insufflation within a body cavity. In this embodiment the device comprises a generally cylindrical body having a proximal end, a distal end, and a longitudinal bore extending from the proximal end to the distal end, the bore being dimensioned to admit a surgical suturing implement thereinto.

The device further comprises a means for anchoring the cylindrical body to skin surrounding the incision at the cylindrical body's proximal end. This anchoring means is dimensioned to restrain the proximal end from entering the incision.

Means are also provided for elevating the anchoring means in a proximal direction. Such an elevation permits a mechanical insufflation of the body cavity, since in use the skin would be elevated away from the body cavity, thereby expanding it for improved visualization.

Affixed within the bore are sealing means. The sealing means has a perforation that is expandable to admit and closely surround the surgical implement. In this way, when the implement is inserted into the incision through the device, insufflation is maintained.

Method for Introducing and Maintaining Insufflation within a Body Cavity during a surgical Procedure As mentioned in the Background section, certain types of surgery are performed within body cavities that have been expanded, which may be achieved by essentially blowing up the area like a balloon.

There is some indication that this may not be the best method of achieving insufflation. In the case of peritoneal surgery, for instance, in which carbon dioxide under pressure is introduced to improve visualization of the operating site by the surgeon, postoperative discomfort typically occurs in the patient until the excess pressure is dissipated. However insufflation is introduced, the opening of an incision can cause a loss of pressure, collapsing the area being operated upon.

A particular embodiment of a method for insufflating a body cavity preparatory to and during a surgical procedure comprises the steps of inserting the device described above into the incision.

Next the device is anchored against the skin surrounding the incision, and the device is elevated, pulling the skin upward and away from the body cavity and thereby insufflating it. A surgical implement is inserted into the bore of the device, which is sealed against pressure leakage, and the surgical procedure can be performed with the surgical implement in the device.

As an alternative, a cannula may be inserted into the bore of the device, in which case the surgical implement is inserted into the cannula. In this case it is preferable that the cannula also have sealing means for maintaining the body cavity gas pressure.

BRIEF DESCRIPTION OF THE DRAWINGS

A preferred embodiment of the invention along with alternate embodiments are described by way of example with reference to the accompanying drawings, in which.

DETAILED DESCRIPTION OF THE PREFERRED EMBODIMENT

Figure 1:
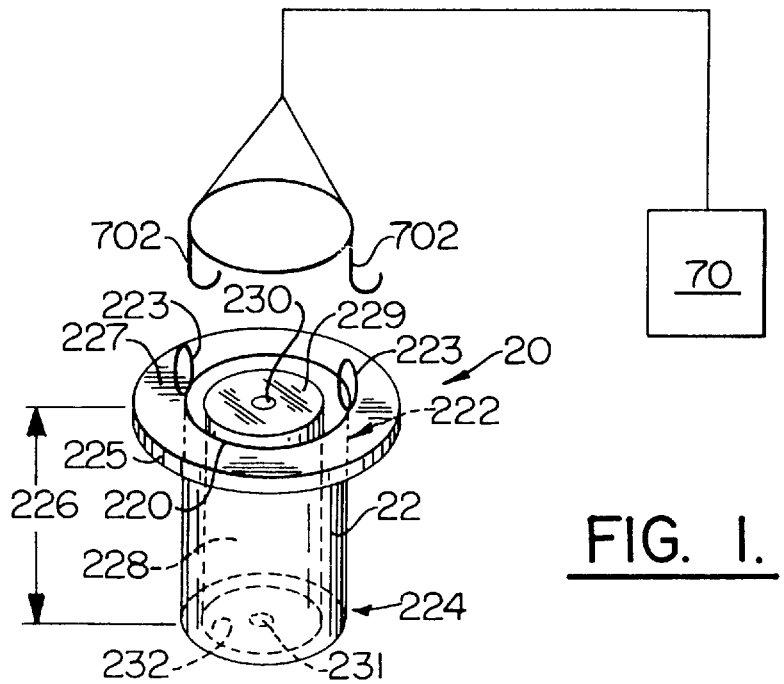
FIG. 1 shows an anchoring device device having a lip.

A description of the preferred embodiments of the present invention will now be presented with reference to FIGS. 1–6. All embodiments, both devices and methods, are directed to the introduction and maintenance of insufflation of a body cavity preparatory to and during an intracavity procedure conducted through a narrow incision.

Device for Insufflating the Body Cavity

This embodiment of the device 20 has several alternate subembodiments illustrated in FIGS. 1–5. This device in its broadest aspect (FIG. 1) comprises a generally cylindrical body 22 that has a proximal end 222, a distal end 224, and a length 226 sufficient to penetrate a predetermined distance into an incision into the body cavity, but insufficient to penetrate into the body cavity. (In other embodiments the length is sufficient to penetrate into the cavity, for instance, when used with a trocar.) Cylindrical body 22 further has a longitudinal bore 228 extending from the proximal end 222 to the distal end 224, which is dimensioned to admit a surgical implement thereinto.

Device 20 also has a lip 227 affixed adjacent the cylindrical body proximal end 222. This lip 227 is dimensioned to restrain the cylindrical body proximal end 222 from entering the incision.

In order to maintain insufflation during insertion of the surgical implement into the incision, sealing means are also provided. In a preferred embodiment, this comprises a gasket 229 affixed within the cylindrical body bore 228, typically adjacent the cylindrical body proximal end 222. The gasket 229 has a perforation 230 that is expandable to admit and closely surround the surgical implement.

The device 22 additionally comprises a second gasket 232 affixed at the cylindrical body distal end 224. Second gasket 232 also has a perforation 231 that is expandable to admit and closely surround the surgical implement.

Another feature of a preferred embodiment of device 22 is an element that permits the device 22 to be anchored to an area of skin surrounding the incision. This enables the surgeon to manipulate surgical implements within the device and to insert and remove them without dislodging the device from the incision. Specifically, the lip 227 comprises means for anchoring the cylindrical body proximal end 222 to the skin. Typically this anchoring is achieved by means associated with the distal surface 225 of the lip 227, which contacts the skin.

In order to achieve a mechanical insufflation of the body cavity, an annulus 220 is affixed to the lip 227 having eyelets 223 into which hooks 702 of a lifting mechanism 70 may be inserted. During a surgical procedure, the lifting mechanism 70, which may comprise any of a number known in the art such as a hydraulic lifter, is attached via the hooks 702 to the annulus 220. Elevation by the lifter 70 pulls the skin upward and expands the size of the body cavity.

The success of such an insufflation is dependent upon the lip's engaging the skin with sufficient adhesion that the elevation thereof does not dissociate them.

Four devices having subembodiments of the anchoring means will be presented in the following.

Annular Patch with Glue

Figure 2:
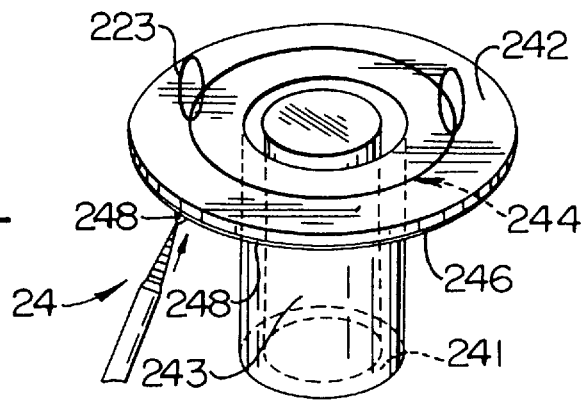
FIG. 2 shows the device having a patch affixable with glue.

In this embodiment, shown in FIG. 2, the device 24 has anchoring means comprising an annular patch 242 affixed in surrounding relation to the cylindrical body 243 proximal end 244 having a distal surface 246 adapted to receive a glue 248 suited for attachment to the skin.

Annular Patch with Adhesive

Figure 3:
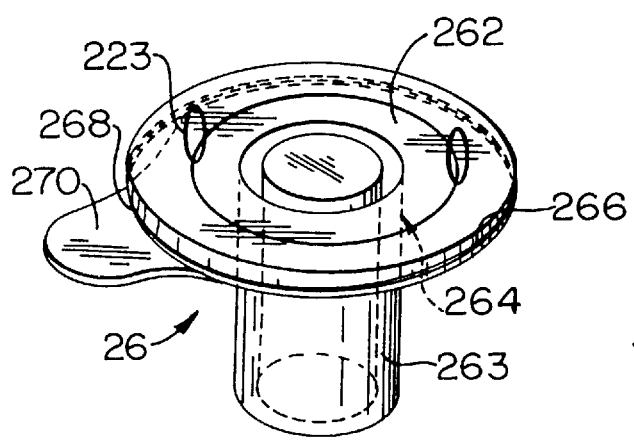
FIG. 3 shows the device having a patch affixable with adhesive.

In this embodiment, shown in FIG. 3, the device 26 has anchoring means comprising an annular patch 262 affixed in surrounding relation to the cylindrical body 263 proximal end 264 having an adhesive material 266 applied to a distal surface 268 for attachment to the skin.

Additionally, this embodiment may further comprise a removable protective sheet 270 covering the adhesive material 266 for shielding the adhesive material 266 until attachment to the skin in desired.

Pincers

In this embodiment, shown in FIG. 4, the device 28 has anchoring means comprising pincer means affixed to and protruding through an annular patch 280 that is affixed in surrounding relation to cylindrical body proximal end 264. The pincer means are here shown as a pair of generally opposed pincer elements 282 and 283, each having a pair of pointed tips 284 and 285, respectively. These pincer elements 282 and device in a similar manner to a clothespin or clamp, being movable between an open position (FIG. 4a) for insertion into the skin and a closed position (FIG. 4b) for pinching the skin. As with a clamp, the pincer elements 282 and 283 are biased to the closed position.

In a particular embodiment, the anchoring means of device 28 further has releasable means for restraining the pincer means in the open position. This feature permits the user to engage the restraining means during insertion of the pincer means into the skin and to release it after insertion, thereby permitting the pincer means to move to the closed position for pinching the skin when desired.

Figure 4A:
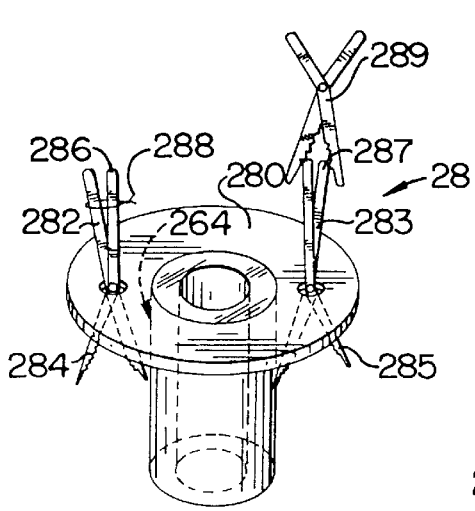
FIG. 4 shows the device anchorable with pincers, with the pincer elements in the (a) open and (b) closed positions. (c) The pincers are restrained by a second annulus having slots shaped to permit opening, release, and reopening. (d) A plan view of the second annulus showing details of one of the slots therein.
Figure 4B:
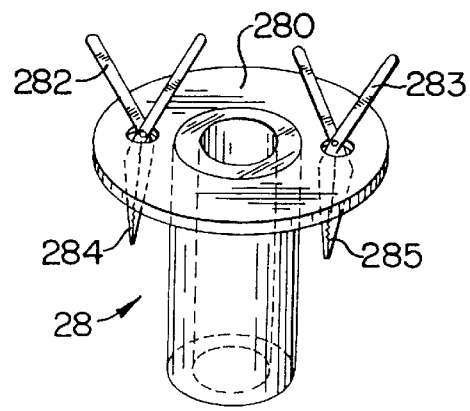

Specifically, the restraining means could comprise a means of keeping the pincer element tops 286 and 287 closely opposed, such as a tie 288 or a clamp 289, as shown in FIG. 4a.

Figure 4C:
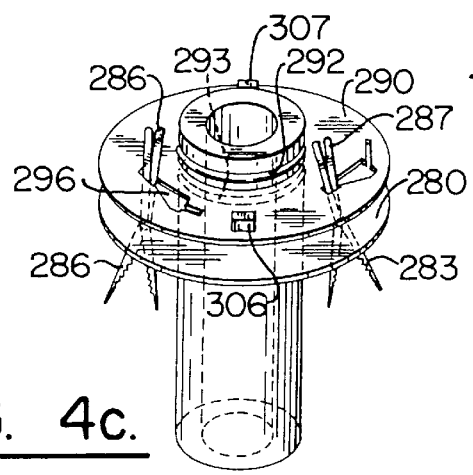
Figure 4D:
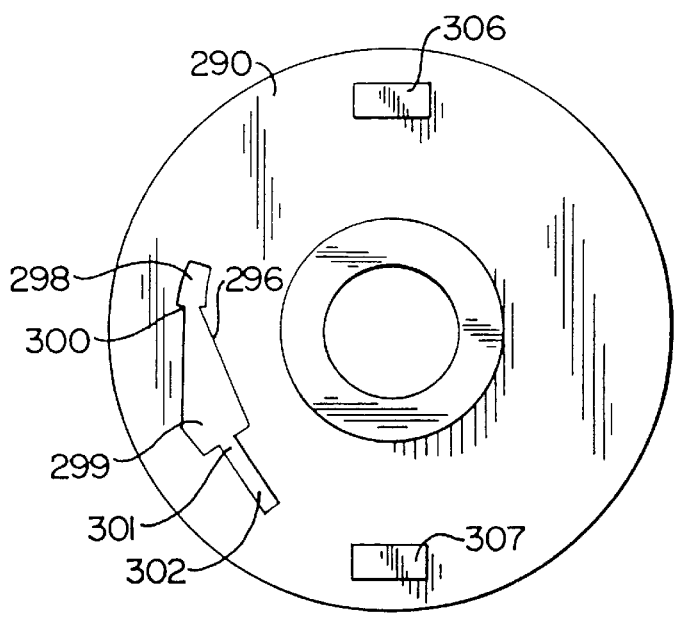

In another embodiment of the restraining means, shown in FIG. 4c, a second annular patch 290 is rotatably affixed in spaced relation above annular patch 280 between first and second shoulders 292,293 on cylindrical body 22. Second annular patch 290 has slots 296 therethrough having a first end 298 dimensioned to restrain pincer element tops 286, 287 together, preventing pincer element tips 284,285 from closing (see FIG. 4d, showing details of a slot 296). Slots 296 further have a central section 299 dimensioned to permit pincer element tops 286,287 to open and thereby to permit pincer element tips 284,285 to close. In use, therefore, anchoring is accomplished by pressing second annular patch 290 until pincer element tips 284,285 penetrate the skin surrounding the incision, and then rotating second annular patch 290 to release the tops 286,287, which allows the tips 284,285 to spring together, pinching the skin. Rotation may be facilitated by upwardly extending protrusions 306,307, against which in use the thumb and forefinger would be placed to rotate second annular patch 290 in a desired direction.

An additional feature is provided to prevent the accidental release of the pincer elements 282,283. Slots 296, in proceeding from the first end 298 to central section 299, have a narrowed region 300 dimensioned smaller than first end 298, for providing a potential energy barrier to the pincer element tops 286,287 moving into the slot's central section 299 prematurely. This barrier is dimensioned to be able to be overcome by finger pressure forcibly rotating the second annular patch 290. Finally, when removal is desired, second annular patch 290 is rotated yet further, ramping pincer element tops 286,287 past second narrowed region 301 into slot second end 302, which is dimensioned sufficiently small to move the pincer elements 282,283 into the open position and permitting them to be removed from the skin.

Opposable Barbs

In this embodiment, shown in FIGS. 5a–e, the device 32 has anchoring means comprising barb means protruding in a distal direction from adjacent the lip 322.

In a specific embodiment, the anchoring means comprises a first ring 34 and a second ring 36. First ring 34 is affixed in surrounding relation adjacent the cylindrical body proximal end 264. The first ring 34 has a first set of barbs 342 having points 344 protruding generally in a distal direction from the distal surface 353. The barbs 342 are canted generally in a first circumferential direction 346 (here, clockwise) with respect to the first ring 34.

Second ring 36 is adapted to engage the first ring 34 rotatably relative thereto. The second ring 36 comprises a second set of barbs 348 having points 350 protruding generally in a distal direction from distal surface 355. The barbs 348 are canted generally in a second circumferential direction 352 (here, counterclockwise) with respect to the second ring 36. Each one of the first set 342 has a complementary one of the second set 348 to form a pair of barbs having their points 344,350 generally opposed. The second ring 36 is further lockable in a position wherein the point 344 of a one barb of the first set 342 is generally adjacent the point 350 of a complementary barb of the second set 348.

In use the first 342 and the second set 348 of barbs are pushed into the skin surrounding the incision, the second ring 36 is rotated to move each one of the complementary pair of barbs adjacent each other, each pair of barbs pinching the skin therebetween, and the second ring 36 is locked to effect anchoring.

In a specific embodiment, first 34 and second 36 rings have opposed camming surfaces 354 and 355, respectively, that represent the proximal 354 and distal 355 surfaces, respectively. Protrusions 358 extending above first ring proximal surface 354 have complementary circumferential slots 356 through second ring 36, the slots 356 dimensioned to have a longer arc length 357 than the length 360 of protrusions 358. The protrusions 358 are dimensioned to have a width 362 closely slidable within the width 364 of slots 356 so that little radial movement is permitted therebetween. In this way first 34 and second 36 rings are relatively rotatable between a first position in which the protrusions 358 are positioned at a first end 366 of the slots 356 and a second position in which the protrusions 358 are positioned at a second end 368 of the slots 356.

First ring 34 further has circumferential slots 370 therethrough, these being offset from second ring slots 356 so as to avoid overlapping second ring slots 356 in either the first or the second position. In the embodiment shown both sets of circumferential slots 356,370 lie generally along a common circumference, although this is not necessary. First ring slots 370 have an arc length 372 generally the same as second ring slot arc length 357.

The first set of barbs 342 distally depend from first ring distal surface 353 and are positioned generally adjacent second ends 374 of slots 370. The second set of barbs 348 distally depend from second ring distal surface 355 and are positioned so as to be generally adjacent first ends 376 of slots 370 when the rings 34,36 are in the first position and further so as to be generally adjacent second ends 374 of slots 370 when the rings 34,36 are in the second position. Therefore, when the rings are rotated from the first to the second position, shown by dotted arrows in FIGS. 5b and 5c, the barb points 344,350 go from being apart to being closely opposed.

In order to facilitate the relative rotation of rings 34,36, handle means are provided on the second ring proximal surface 351. Specifically, handle means comprise a pair of generally radially opposed upwardly extending knobs 378 that, when pushed, effect the desired rotation.

As mentioned, means are provided for locking the rings 34,36 against rotation when in the second position. This may be accomplished, in one embodiment, by having at least one of the knobs 378 further comprise a distally extending screw 380 that mates with a threaded bore 382 through second ring 36. When the rings 34,36 are in the second position, second ring threaded bore 382 communicates with first ring threaded bore 384, and, by screwing knob 378 beyond bore 382 into bore 384, locking between the rings 34,36 is effected.

In order to prevent barb points 344,350 from injuring the user, the anchoring means further comprises releasable protective means for covering the barb points 344,350 until use is desired. In a simple embodiment, device 32 may be parked in a foam-type holder until needed. Another embodiment, however, is contemplated in which the protective means is a part of the device 32.

Figure 5A:
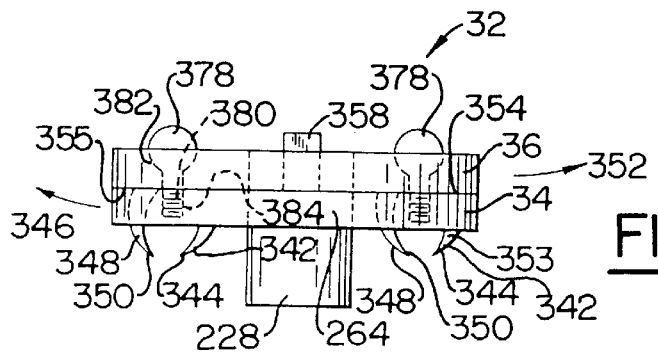
FIG. 5 shows the device anchorable with complementary pairs of barbs depending from coaxial rings, the device shown in (a) side view; (b) plan view; and (c) bottom view. (d) Means for protecting the user against accidental injury from the barb points are shown that include a third circumferential ring movably affixed to the first ring. The insufflation mechanism is also illustrated. (e) This embodiment has windows permitting access to tissue surrounding the incision and to the edges of the incision.
Figure 5B:
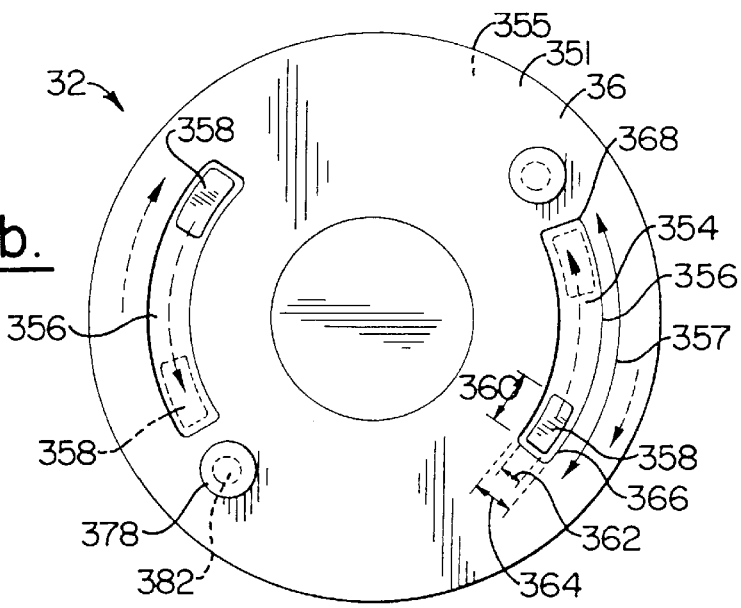
Figure 5C:
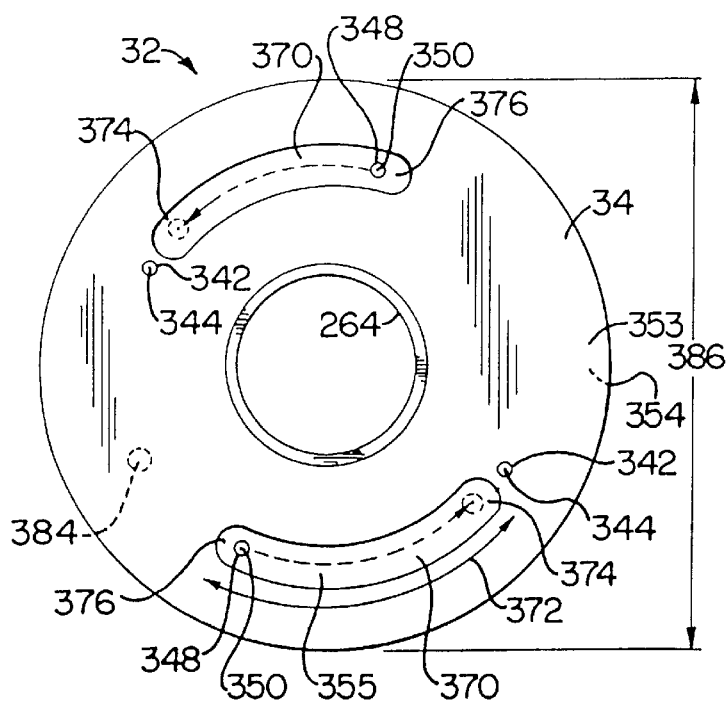
Figure 5D:
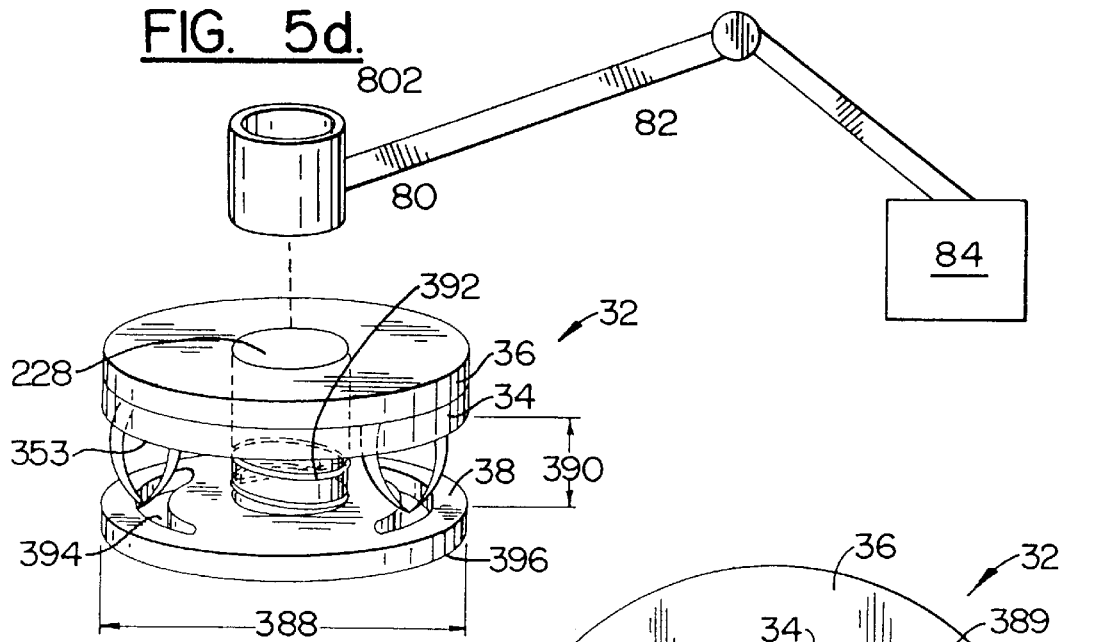

In this subembodiment, shown in FIG. 5d, a third ring 38 is provided that is movably affixed in spaced relation to first ring 34 and that has a diameter 388 generally the same as the diameter 386 of first ring 34. Third ring 38 is biased via spring 392, which is affixed at one end to first ring 34 and at another end to third ring 38, to be axially separated from first ring 34 by a distance at least equal to the axial extent 390 of the barbs 342,348 in a distal direction from the first ring distal surface 353.

Third ring 38 additionally has circumferential slots 394 therethrough that have an arc length at least sufficient to permit barbs 342,348 to protrude therethrough, as shown in FIG. 5d. A compression of spring 392, to bring first 34 and third 38 rings into proximity, thus exposes the barb points 344,350, permitting them to be inserted into skin. In use, then, a release of the protective means, the third ring 38, is accomplished by placing the third ring distal surface 396 against the skin and pushing down on second ring 36, causing spring 392 to compress, permitting barbs 342,348 to protrude through third ring slots 394, and then to enter the skin.

In a subembodiment, cylindrical body 22 is sufficiently long to penetrate into the incision, and can itself act as a trocar.

Figure 5E:
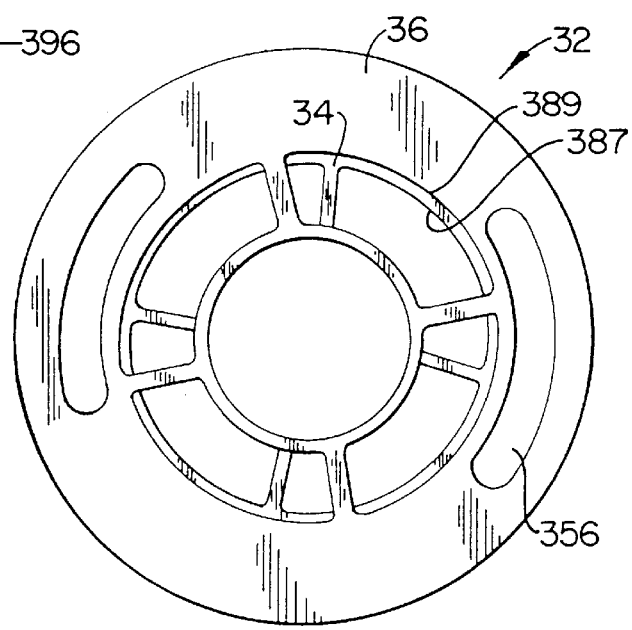

In order to provide access through the device 32, the first ring 34 has four windows 387 therethrough from the proximal 353 to the distal 354 surface; similarly, the second ring 36 has four windows 389 therethrough from the proximal 351 to the distal 355 surface (see FIG. 5e). Windows 387,389 are positioned to communicate at least partially, whether the first 34 and the second 36 rings are in the first or the second position. These windows are for permitting access to the tissue surrounding the incision and to the sides of the incision, providing the possibility of manipulating implements therethrough.

The insufflation mechanism for this embodiment of the device is also shown in FIG. 5d. Here the elevating means comprises a second annulus 80 having a bore 802. This second annulus 80 is affixable to the second ring 36 by any of a number of methods well known in the art, such as via bayonet mount (twist to lock). The second annulus' bore 802 communicates with the cylindrical body bore 228 and is also dimensioned to admit a surgical implement.

To the second annulus 80 is affixed an arm 82, which is couplable to a lifting mechanism such as a mechanical lifter 84 for lifting the second annulus 80 in the proximal direction to achieve insufflation.

Method for Insufflating a Body Cavity

Figure 6A:
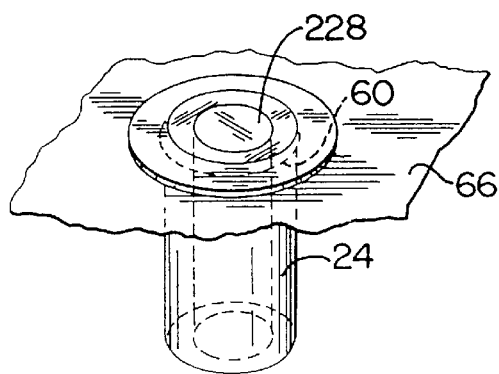
FIG. 6 shows the method of using the device of FIG. 5, which includes (a) inserting the device into the incision and anchoring it against the skin; (b) elevating the device to insufflate the body cavity; and (c) inserting and using a surgical implement. An alternate embodiment includes (d) inserting a cannula into the device bore; and (e) inserting the surgical implement into the cannula.
Figure 6C:
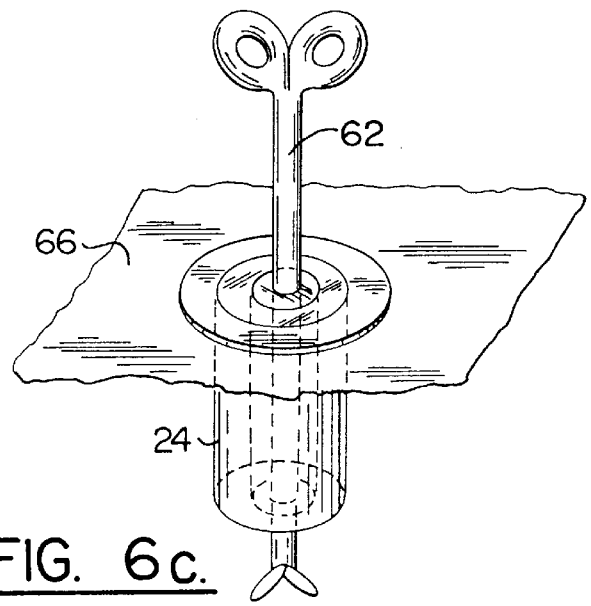
Figure 6D:
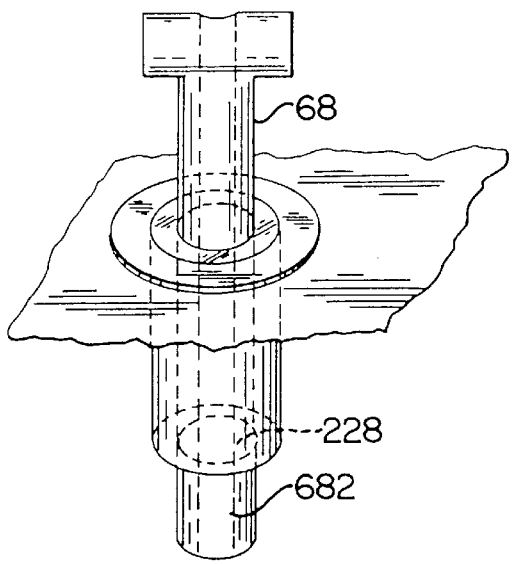

The method utilizing a device 24, as shown in FIG. 6, comprises inserting the device 24 into the incision 60 and anchoring it against skin 66 surrounding the incision 60 (FIG. 6a). Next the device 24 is elevated using the hooks 702, which are lifted by hydraulic lifter 70 (FIG. 6b). Then a surgical implement 62 is inserted into the device bore 228, and the surgical procedure is performed with the surgical implement 62 (FIG. 6c).

Figure 6E:
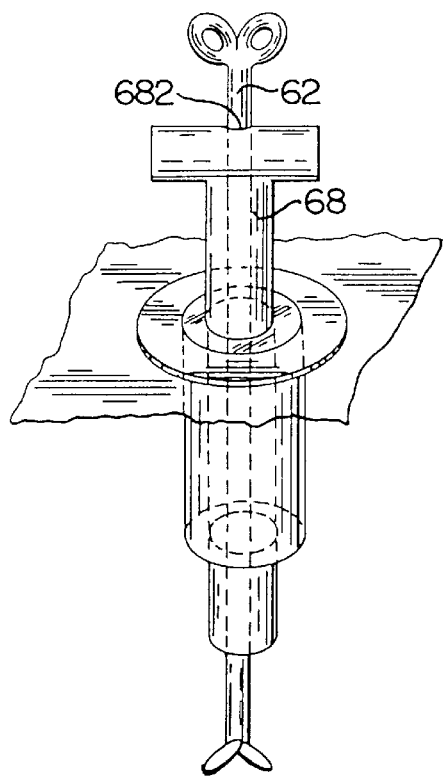
Figure 6B:
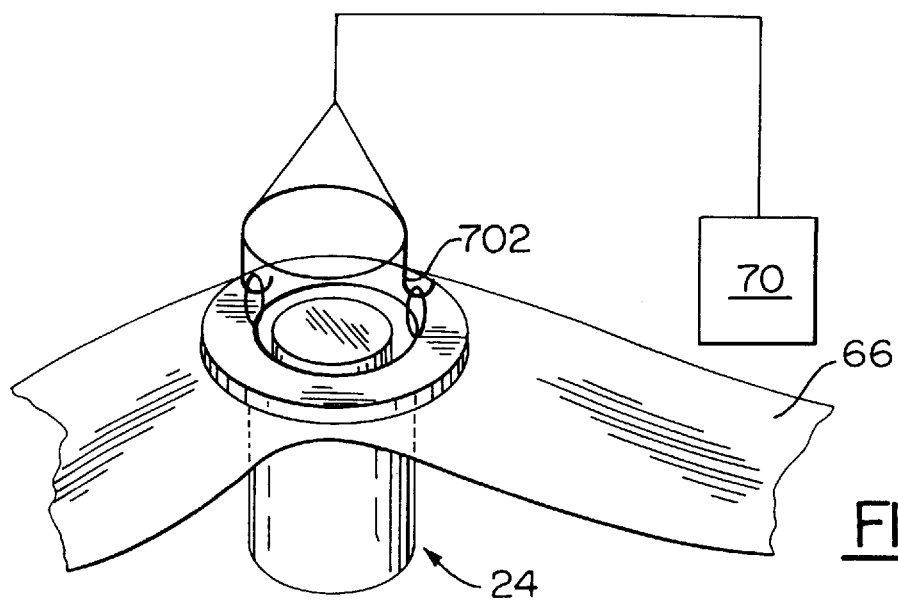

A related embodiment has the additional step, following the anchoring step, of inserting a cannula 68 into the device bore 228 (FIG. 6d), and wherein the surgical implement inserting step comprises inserting the surgical implement 62 into the cannula bore 682 (FIG. 6e).

It may be appreciated by one skilled in the art that additional embodiments may be contemplated, including other means of deploying and positioning the suture needle and other methods for using the apparatus.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

What is claimed is:

1. A device for insufflating a body cavity preparatory to and during an intracavity procedure, the device comprising:

a generally cylindrical body having:

a proximal end;

a distal end; and a longitudinal bore extending from the proximal end to the distal end, the bore dimensioned to admit a surgical implement thereinto;

means for anchoring the cylindrical body to skin surrounding the incision generally adjacent the cylindrical body proximal end, the anchoring means dimensioned to restrain the cylindrical body proximal end from entering the incision;

sealing means affixed within the cylindrical body bore, the sealing means having a perforation expandable to admit and closely surround the surgical implement for maintaining insufflation during insertion of the surgical implement into the incision; and means mechanically coupled to the anchoring means for elevating the anchoring means in a proximal direction, thereby permitting a mechanical insufflation of the body cavity.

2. The device recited in claim 1, wherein the anchoring means comprises a generally annular member affixed in surrounding relation to the cylindrical body generally adjacent the cylindrical body proximal end, the annular member having a distal surface adapted to engage the skin surrounding the incision with sufficient adhesion that the annular member and the skin remain engaged during a mechanical insufflation of the body cavity by the elevating means.

3. The device recited in claim 2, wherein the sealing means comprises:

a first gasket affixed adjacent the cylindrical body proximal end; and a second gasket affixed adjacent the cylindrical body distal end.

4. The device recited in claim 2, wherein the anchoring means comprises an annular patch affixed in surrounding relation to the cylindrical body proximal end having a distal surface adapted to receive a glue suited for attachment to the skin.

5. The device recited in claim 2, wherein the anchoring means comprises an annular patch affixed in surrounding relation to the cylindrical body proximal end having an adhesive material applied to a distal surface for attachment to the skin.

6. The device recited in claim 5, wherein the patch further comprises a removable protective sheet covering the adhesive material for shielding the adhesive material until attachment to the skin in desired.

7. The device recited in claim 2, wherein the anchoring means comprises pincer means protruding from the annular member distal surface, the pincer means having a pair of pointed tips, the pincer means movable between an open position for insertion into the skin and a closed position for pinching the skin, the pincer means biased to the closed position.

8. The device recited in claim 7, wherein the anchoring means further comprises releasable means for restraining the pincer means in the open position, wherein in use the restraining means is engaged during insertion of the pincer means into the skin and is released after insertion of the pincer means into the skin to permit the pincer means to move to the closed position for pinching the skin.

9. The device recited in claim 2, wherein the anchoring means comprises barb means protruding in a distal direction from the anchoring means.

10. The device recited in claim 9, wherein the elevating means comprises a second annular member having a bore, the second annular member affixable to the anchoring means annular member, the second annular member bore communicating with the cylindrical body bore and dimensioned to admit a surgical implement thereinto.

11. The device recited in claim 10, wherein the elevating means further comprises an arm affixed to the second annular member, the arm couplable to a lifting mechanism for lifting the second annular member in the proximal direction.

12. The device recited in claim 2, wherein the annular member comprises:

a first ring affixed in surrounding relation adjacent the cylindrical body proximal end, the first ring comprising a first set of barbs having points protruding generally in a distal direction therefrom, the barbs canted generally in a first circumferential direction with respect to the first ring;

a second ring adapted to engage the first ring rotatably relative thereto, the second ring comprising a second set of barbs having points protruding generally in a distal direction therefrom, the barbs canted generally in a second circumferential direction with respect to the second ring, each one of the first set having a complementary one of the second set to form a pair of barbs, the second ring lockable in a position wherein the point of a one barb of the first set is generally adjacent the point of a complementary barb of the second set;

wherein in use the first and the second set of barbs are pushed into the skin surrounding the incision, the second ring is rotated to move each one of the complementary pair of barbs adjacent each other, each pair of barbs pinching the skin therebetween, and the second ring is locked to effect anchoring.

13. The device recited in claim 12, wherein the elevating means comprises a second annular member having a bore, the second annular member affixable to the second ring, the second annular member bore communicating with the cylindrical body bore and dimensioned to admit a surgical implement thereinto.

14. The device recited in claim 13, wherein the elevating means further comprises an arm affixed to the second annular member, the arm couplable to a lifting mechanism for lifting the second annular member in the proximal direction.

15. The device recited in claim 14, wherein the anchoring means further comprises releasable protective means for covering the barb points until use is desired.

16. The device recited in claim 14, wherein the anchoring means further comprises handle means affixed to the second ring for facilitating the rotation of the second ring during use.

17. The device recited in claim 12, wherein:

the first ring has a window therethrough from a proximal surface to a distal surface;

the second ring has a window therethrough from a proximal surface to a distal surface; and the windows in the first and the second ring communicate at least partially irrespective of the amount of relative rotation between the first and the second ring, the windows for permitting access between the incision and the cylindrical body and to tissue surrounding the incision.

18. A method for insufflating a body cavity preparatory to and during a surgical procedure using a narrow incision for access into the body cavity, the method comprising the steps of:

inserting a device into the incision, the device comprising a generally cylindrical body having:
a proximal end;
a distal end; and
a longitudinal bore extending from the proximal end to the distal end, the bore dimensioned to admit a surgical implement thereinto;

anchoring the cylindrical body to skin surrounding the incision generally adjacent the cylindrical body proximal end to restrain the cylindrical body proximal end from entering the incision;

elevating the cylindrical body in a proximal direction, thereby mechanically insufflating the body cavity;

sealing the bore with sealing means having a perforation expandable to admit and closely surround the surgical implement for maintaining insufflation during insertion of the surgical implement into the incision;

inserting a surgical implement into the bore of the device; and performing the surgical procedure with the surgical implement.

19. The method recited in claim 18, further comprising the step, following the anchoring step, of inserting a cannula into the bore of the device, and wherein the surgical implement inserting step comprises inserting the surgical implement into the cannula.

* * * * *